(12) United States Patent
Frampton et al.

(10) Patent No.: US 11,116,655 B2
(45) Date of Patent: Sep. 14, 2021

(54) EXPANDABLE OSTOMY BAG

(71) Applicant: Welland Medical Limited, Crawley (GB)

(72) Inventors: Kim Frampton, Crawley (GB); Paul Bird, Crawley (GB)

(73) Assignee: Welland Medical Limited, Crawley (GB)

( * ) Notice: Subject to any disclaimer, the term of this patent is extended or adjusted under 35 U.S.C. 154(b) by 867 days.

(21) Appl. No.: 14/907,204

(22) PCT Filed: Jul. 23, 2014

(86) PCT No.: PCT/EP2014/065802
§ 371 (c)(1),
(2) Date: Jan. 22, 2016

(87) PCT Pub. No.: WO2015/011182
PCT Pub. Date: Jan. 29, 2015

(65) Prior Publication Data
US 2016/0151198 A1      Jun. 2, 2016

(30) Foreign Application Priority Data

Jul. 23, 2013   (GB) ..................... 1313143

(51) Int. Cl.
*A61F 5/448*    (2006.01)
*A61F 5/44*     (2006.01)
*A61F 5/445*    (2006.01)

(52) U.S. Cl.
CPC ............ *A61F 5/448* (2013.01); *A61F 5/4404* (2013.01); *A61F 5/445* (2013.01)

(58) Field of Classification Search
CPC combination set(s) only.
See application file for complete search history.

(56) References Cited

U.S. PATENT DOCUMENTS

| | | | | |
|---|---|---|---|---|
| 2,496,175 A | * | 1/1950 | Murle Perry | A61F 5/445 604/335 |
| 4,411,659 A | * | 10/1983 | Jensen | A61F 5/441 604/332 |
| 4,790,833 A | * | 12/1988 | Schmidt | A61M 1/0019 604/317 |
| 4,950,223 A | * | 8/1990 | Silvanov | A61F 5/441 128/DIG. 25 |
| 5,348,546 A | * | 9/1994 | Norton | A61F 5/445 604/332 |
| 5,549,587 A | * | 8/1996 | Norton | A61F 5/441 604/333 |

(Continued)

FOREIGN PATENT DOCUMENTS

| | | | | |
|---|---|---|---|---|
| GB | 2518855 A | * | 4/2015 | ............ A61F 5/445 |
| WO | 87/01932 A1 | | 4/1987 | |

OTHER PUBLICATIONS

International Search Report and Written Opinion for PCT/EP/065802, dated Oct. 17, 2014.

*Primary Examiner* — Guy K Townsend
(74) *Attorney, Agent, or Firm* — Foley Hoag LLP

(57) ABSTRACT

An ostomy bag has an inlet leading to a waste collection space defined by two opposing surfaces of two walls. The opposing surfaces are configured to separate on the introduction of waste through the inlet and in at least one of the walls there is at least one corrugation.

13 Claims, 4 Drawing Sheets

(56) References Cited

U.S. PATENT DOCUMENTS

| | | | | |
|---|---|---|---|---|
| 6,050,982 | A * | 4/2000 | Wheeler | A61F 5/445 600/29 |
| 6,712,800 | B2 * | 3/2004 | Kanbara | A61F 5/441 604/333 |
| 6,723,079 | B2 * | 4/2004 | Cline | A61F 5/445 128/887 |
| 7,789,866 | B2 * | 9/2010 | Poulsen | A61F 5/441 604/333 |
| 8,100,875 | B2 * | 1/2012 | Cline | A61F 5/445 604/328 |
| 2003/0014023 | A1 * | 1/2003 | Kanbara | A61F 5/441 604/333 |
| 2006/0253091 | A1 * | 11/2006 | Vernon | A61F 5/4405 604/353 |
| 2007/0088300 | A1 * | 4/2007 | Cline | A61F 5/445 604/342 |
| 2008/0306459 | A1 * | 12/2008 | Albrectsen | A61F 5/441 604/333 |
| 2009/0227973 | A1 * | 9/2009 | Worsoee | A61F 5/441 604/333 |
| 2012/0179124 | A1 * | 7/2012 | Nguyen-Demary | A61F 5/445 604/333 |
| 2015/0190271 | A1 * | 7/2015 | Chang | A61F 5/445 604/332 |
| 2016/0151198 | A1 * | 6/2016 | Frampton | A61F 5/448 604/340 |

* cited by examiner

Profile 1
(To suit upper pouch profile)

Profile 2
(To suit lower pouch profile)

Profile 3
(To suit full pouch profile)

EXPANDABLE OSTOMY BAG

This application is the U.S. National Stage Entry of International Patent Application number PCT/EP2014/065,802, filed 23 Jul. 2014, entitled "Expandable Ostomy Bag," which claims priority to UK Patent Application number 1313143.8 filed 23 Jul. 2013.

The present invention relates to an ostomy bag for collection of waste from a human or animal body. In particular the invention provides an expandable ostomy bag.

BACKGROUND OF THE INVENTION

Ostomy bags are medical devices that are worn by an individual and they can be used for the collection of waste from a surgically diverted bowel or urinary system of the individual. They are used to collect waste that is output from a stoma created in the ostomate's skin and connected to the intestine or urinary system.

Known ostomy bags comprise a collection bag and in some cases the collection bag is attached mechanically or with adhesive to a mounting plate, commonly referred to as a wafer or a baseplate. The mounting plate is fixed to the skin of an individual and the ostomy bag allows the waste to drain from a stoma into the collection bag, while protecting the surrounding skin from contamination by the waste.

Ostomy bags should be air- and water-tight and they should allow the individual to lead an active normal lifestyle that can include all forms of sports and recreation. However, there is a need to make ostomy bags discrete.

The need to provide discrete ostomy bags must be balanced with the need to provide a sufficiently large collection bag so that unexpected deposits can be accommodated by the bag. For example, if an individual suffers from an upset bowel, the bag should not overflow. Typically, ostomy bags are emptied at least once per day.

The present invention seeks to provide an ostomy bag which addresses one or more of the problems presented by prior art arrangements. In particular, the present invention seeks to provide an ostomy bag which is discrete.

SUMMARY OF THE INVENTION

Remarkably, it has now been found that an ostomy bag can be provided that is expandable. This provides the advantage that an ostomy bag can be provided that has a smaller and more discrete appearance than known ostomy bags, but it is capable of containing the same volume as larger known ostomy bags. It provides the additional advantage that less material is needed to produce an ostomy bag capable of containing the same volume as larger known ostomy bags.

In accordance with the present invention, there is provided an ostomy bag having an inlet leading to a waste collection space defined by two opposing surfaces of two walls, the opposing surfaces configured to separate on the introduction of waste through the inlet and including in at least one of the walls at least one corrugation.

Preferably, the walls are welded together at their edges.

Preferably, a mounting plate abuts the inlet.

Preferably, the at least one corrugation is provided in the wall opposing the inlet.

Preferably, no corrugation is provided in the wall defining the inlet. This provides the advantage that the body facing surface of the ostomy bag sits flush against the skin of a user and thereby provides a discrete appearance.

Preferably, the corrugation comprises a ridge in a first wall of the bag which extends outwardly away from the opposing surface of the bag. More preferably, in cross section, the corrugation comprises a smooth sinusoidal wave in the first wall of the bag.

Preferably, the corrugation is deformable under the weight of waste in the bag. Advantageously, when the bag fills, deformation of the corrugation allows the opposing surfaces of the bag to separate, thereby expanding the apparent size of the bag.

Preferably, the corrugation is substantially parallel with the edge of the opposing surfaces of the bag.

Preferably, the bag has an upper portion near a top and lower portion near a bottom of the bag. Preferably, the corrugation is located proximal to the bottom of the bag and distal to the top of the bag. This has the effect that the opposing surfaces of the bag are capable of separating more from each other at the lower portion of the bag.

Advantageously, the bag fills from the bottom and this encourages flow of deposit into the bag and assists with reduction of pancaking. Pancaking is a term used to describe the situation where large quantities of soft waste are deposited with speed to the inlet of a clean ostomy bag, they stick to the immediately opposing inner surface of the bag, blocking the inlet and preventing use of space distanced from the outlet. As a consequence of pancaking, despite there being available capacity in the bag, the bag can overflow when subsequent deposits are attempted. The present invention seeks to provide an ostomy bag which inter alia reduces the occurrence of pancaking.

More preferably, the corrugation is approximately arcuate and is located in a sector defined in the lower portion of the bag.

Even more preferably, the walls of the bag are defined by an ellipse, having an upper focus, a lower focus, an upper vertex and a lower vertex. Preferably the corrugation is located in the major sector of the ellipse wherein the sector is approximately defined by a chord through the upper focus. More preferably, the top of the sector is defined by two lines extending from the upper focus to points equidistant from the upper vertex and wherein the lines are above a chord through the upper focus.

Preferably, the inlet leading to a waste collection space is approximately aligned with the upper focus.

Preferably, the corrugation comprises a ridge or wave having a height of about 5 mm and a width of about 5 mm. Preferably, in cross section, the ridge or wave is approximately defined by a circular sector. More preferably, the height of the ridge or wave tapers from a maximum height proximal to the lower vertex or bottom of the bag to a minimum height distal to the lower vertex or bottom of the bag. Preferably, the ridge or wave tapers to a minimum height of zero.

Preferably, a plurality of parallel corrugations are provided. Preferably, about three to about seven corrugations are provided. Most preferably, about four corrugations are provided. Preferably, in cross section, the corrugations provide a continuous sinusoidal curve.

Preferably, the corrugations are formed by vacuum forming. In one embodiment 100 micron film with a 5 mm draw capability is subjected to vacuum forming.

Advantageously, despite the corrugations being formed by vacuum forming, the odour barrier of the bag remains intact.

The bag is preferably of polyethylene fabric. Woven or non-woven fabric can be used, including materials such as Lycra®.

The amount of material included in the corrugation can be varied depending on capacity required for the bag. Conveniently the corrugations provide 30-50% of the overall surface of the bag wall in which it is provided.

The walls of the collection bag may comprise any conventional structure known in the prior art. In one preferred option, the bag comprises a laminate which has hydrophobic exposed surfaces and degradable core and means for delaminating the bag whereby to expose the degradable core and facilitate easy flushing of the bag after use.

In an alternative option, the bag comprises a disposable or degradable liner enclosed in a hydrophobic bag and means for conveniently removing the liner for disposal.

In another option, the bag may further include in an accessible wall a closable exit aperture and means for selectively releasing accumulated gas through the aperture.

The exit aperture can conveniently be resealably opened by a closure which covers the aperture and attaches to the bag by means of a peelable adhesive. The closure may conveniently be provided in the form of a sealing flap which folds down from a seam around the edge of the bag. Alternatively, the closure may comprise a patch which can be completely detached from the bag and optionally replaced with another. Alternative resealable means to a peelable adhesive will no doubt occur to the skilled addressee and include, without limitation, a mechanical seal comprising an annular rib received in an annular groove or a suction based closure means; Velcro® or similar.

In use, when ballooning occurs, the user can discreetly remove the closure, gently squeeze the bag and release gas to return the bag to a comfortable size.

In other options, a valve might be used to close the exit aperture, the valve being easily activated by the user, for example by depressing or nipping an area around the aperture.

BRIEF DESCRIPTION OF THE DRAWINGS

One embodiment of a bag in accordance with the invention is now described with reference to the accompanying figures of which.

DETAILED DESCRIPTION OF THE INVENTION

It will be appreciated that aspects, embodiments and preferred features of the invention have been described herein in a way that allows the specification to be written in a clear and concise way. However, unless circumstances clearly dictate otherwise, aspects, embodiments and preferred features can be variously combined or separated in accordance with the invention. In a preferred embodiment, a device in accordance with the invention comprises all aspects of the invention.

Within the context of this specification, the word "about" means preferably plus or minus 20%, more preferably plus or minus 10%, even more preferably plus or minus 5%, most preferably plus or minus 2%.

Within the context of this specification, the word "comprises" means "includes, among other things" and should not be construed to mean "consists of only".

Within the context of this specification, the word "substantially" means preferably at least 90%, more preferably 95%, even more preferably 98%, most preferably 99%.

Within the context of this specification, the word expandable and the word expansible are taken to mean capable of being expanded. In this regard, the corrugations of ostomy bags according to the invention are capable of being spread or opened to enlarge or increase the apparent size of the ostomy bags.

Figure 1:
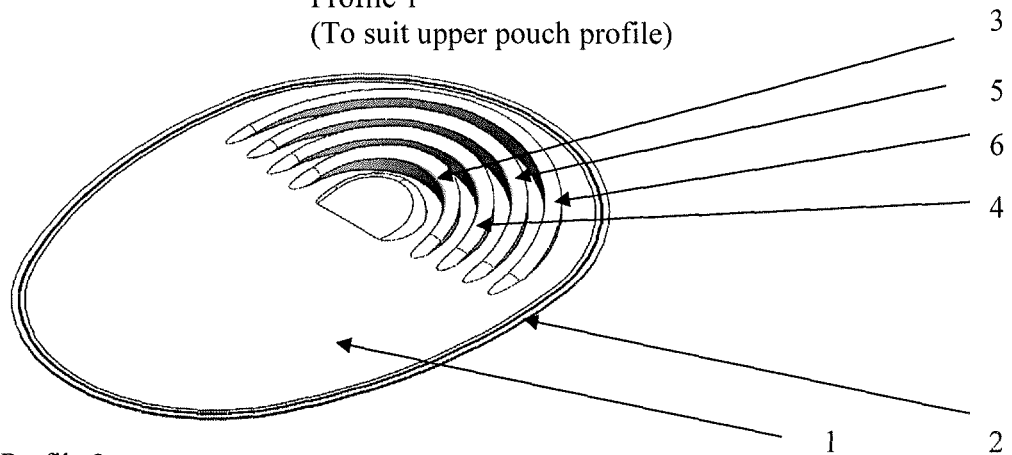
FIG. 1 shows profile types of some ostomy bags according to the invention. It will be appreciated that other profile types not specifically shown also fall within the invention.
Figure 1:
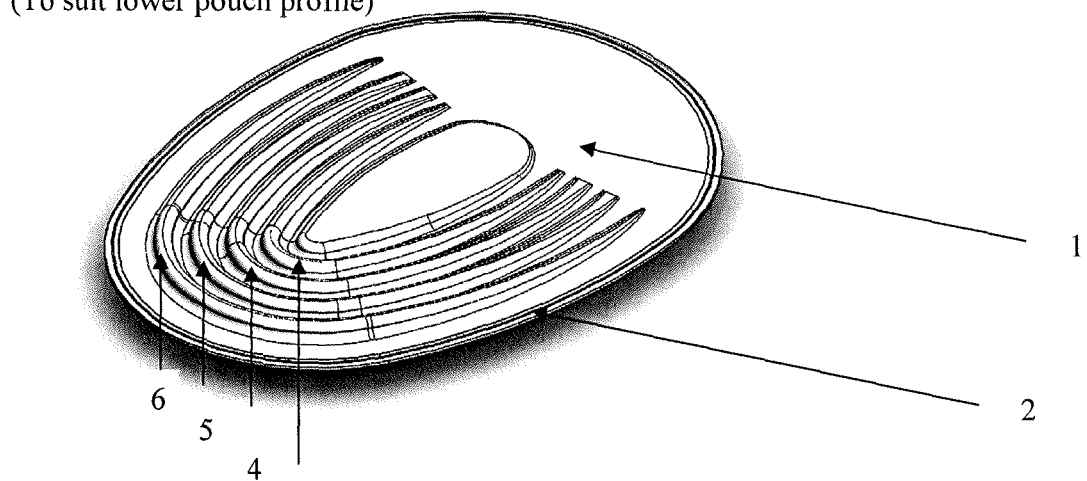
Figure 1:
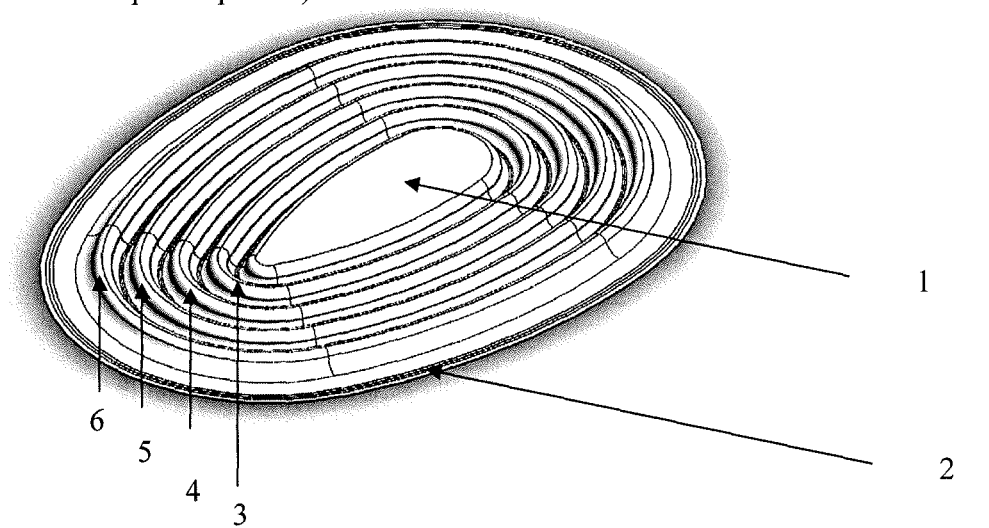

Corrugations can be formed in a wall of an elliptical bag by vacuum forming. It will be appreciated that an elliptical bag is specifically exemplified, but bags having alternative configurations fall within the scope of the invention. For example, in an alternative embodiment the invention provides a rectangular bag. As shown in FIG. 1, the corrugations can be made in various profiles including "Profile 1" to suit an upper pouch profile, "Profile 2" to suit a lower pouch profile and "Profile 3" to suit full pouch profile.

According to the invention, the bag can be a closed bag, or a drainable bag having an opening through which the bag may be drained.

FIG. 1 shows one wall 1 of two opposing walls of an eliptical ostomy bag defining internally opposing surfaces. The walls are welded together along a seam 2. Four corrugations 3, 4, 5, 6 are provided in the wall 1 by vacuum forming. In this process the wall is subjected to heat and vacuum simultaneously. Typically, a sheet of film is heated to a forming temperature, stretched onto or into a single-surface mold, and held against the mold by applying a vacuum between the mold surface and the sheet. The corrugations provide a deformable wall 1 which ensures that the opposing surfaces forming a waste collection space separate from each other when the bag is filled.

Figure 2:
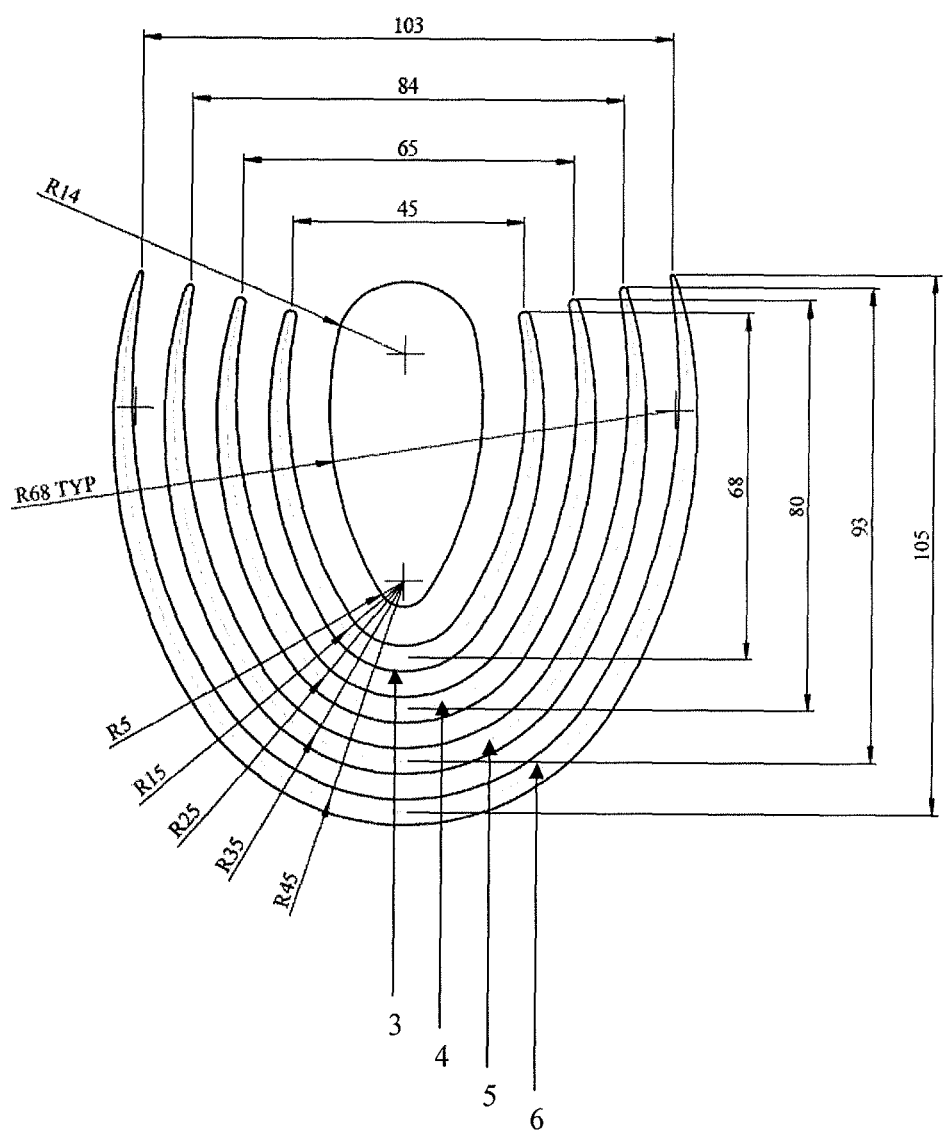
FIG. 2 shows a view of an ostomy bag according to the invention. The drawing shows four corrugations and an example of possible dimensions of the corrugations. It will be appreciated that other numbers of corrugations and dimensions fall within the scope of the invention.

FIG. 2 shows preferred dimensions of the corrugations 3, 4, 5, 6.

Figure 3:
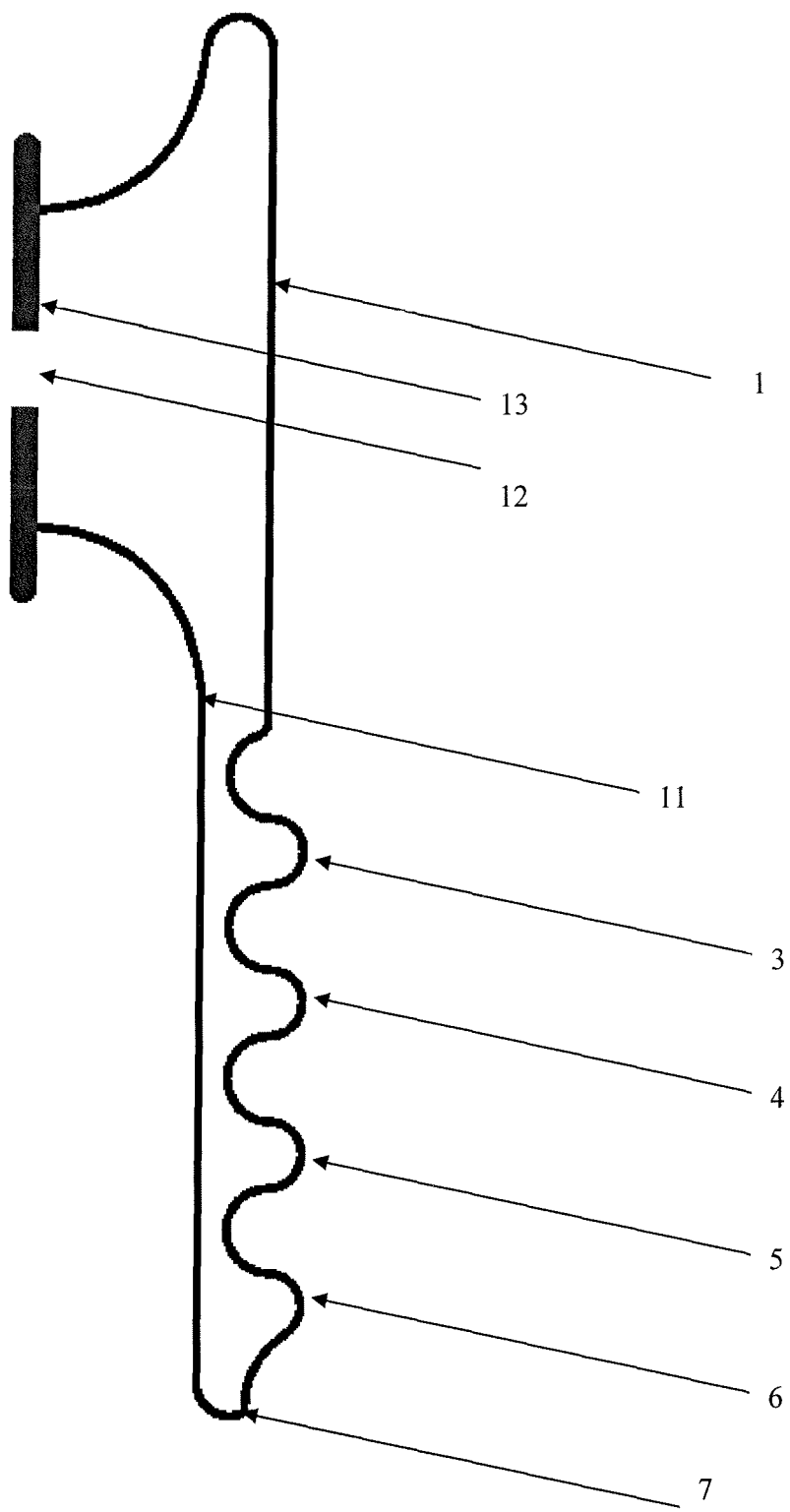
FIG. 3 shows a cross sectional side view of an ostomy bag according to the invention in an empty state.

As can be seen from the cross section shown in FIG. 3, one wall 11 of the ostomy bag has an inlet 12 in the face of the wall. A mounting plate 13 abuts the inlet. In use, deposits into the ostomy bag enter through the mounting plate 13 and the inlet 12. The opposing wall 1, has four corrugations 3, 4, 5, 6 located proximal to the lower vertex 7 of the bag. It will be appreciated that four corrugations are specifically exemplified, but bags having alternative numbers of corrugations fall within the scope of the invention. For example, in an alternative embodiment the invention provides an ostomy bag having three or five corrugations.

Figure 4:
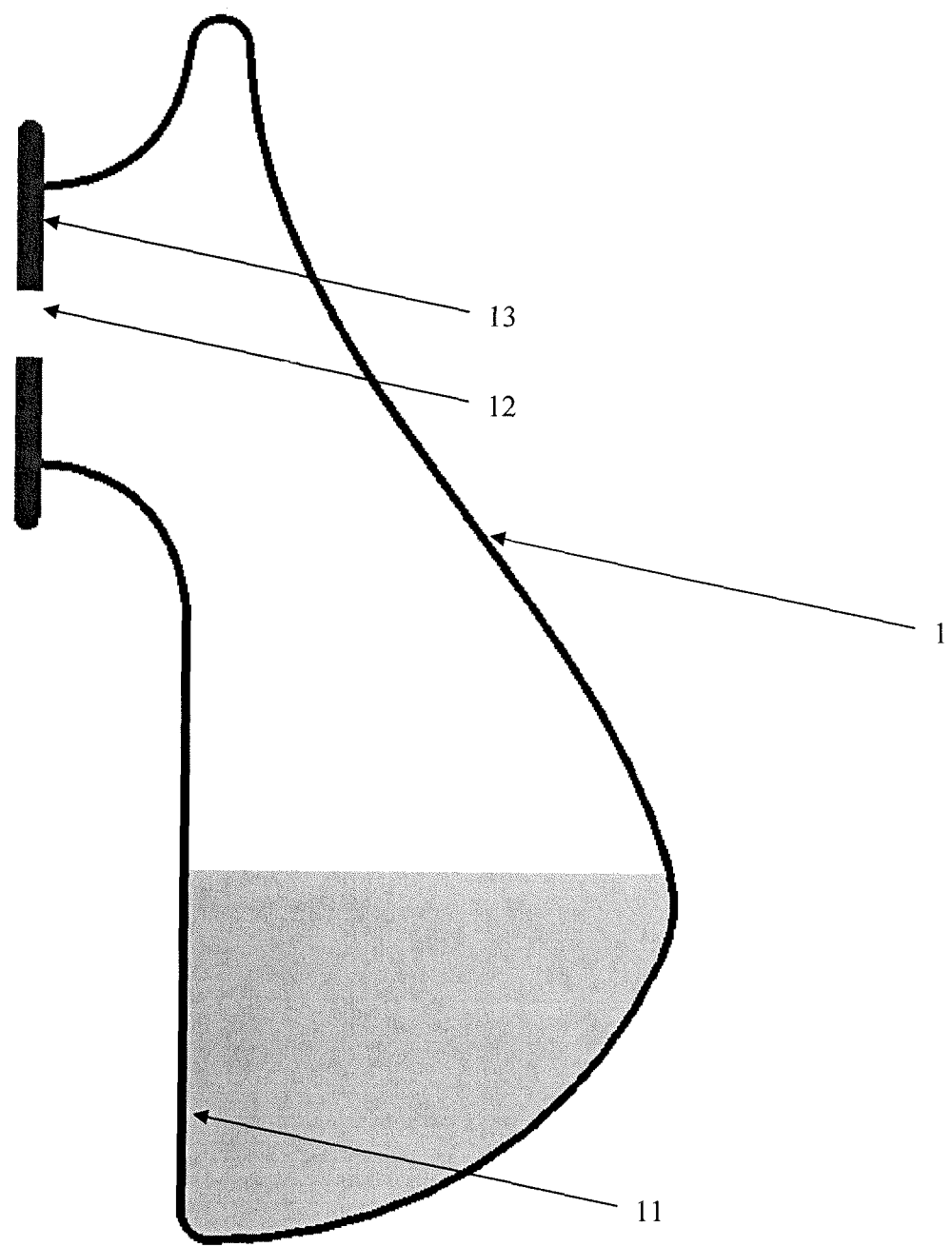
FIG. 4 shows a cross sectional side view of an ostomy bag according to the invention in a filled state.

As shown in FIG. 4, when the bag is filled, the corrugations 3, 4, 5, 6 deform and the opposing surfaces of walls 1, 11 separate.

To test a embodiments of the invention after vacuum forming, odour testing of vacuum formed films was carried out with variants in setting, heat application and profile type. Details of the test are described below:

Purpose of Evaluation

To carry out an odour analysis of a film having a thickness of 100 µm vacuum formed to a 10 mm depth of draw.

Conclusion

The odour barrier layer of the film having a thickness of 100 µm has become compromised by vacuum forming to a 10 mm draw depth. Onion odour was detected between the two and the three hour test interval.

Samples

The samples tested are shown in Table 1.

In the table, "Sample" corresponds to the numbering of the sample. "Ref" corresponds to a reference for each sample. "Profile Type" corresponds to the profile types shown in FIG. 1. "Description" corresponds to a short description of the sample.

TABLE 1

| Sample | Ref | Profile Type | Description |
|---|---|---|---|
| 1 | A | 2 | Film |
| 2 | D | 2 | Film |
| 3 | E | 2 | Film |

TEST METHOD AND PROGRAM

Odour Test

Determination of odour transmission of colostomy and ileostomy bags (tested in accordance with the standard test described in BS IS08670-3:2000) was conducted.

Onion Odour Test

Samples of onion (20.0 g+/−2 g) were placed in the bottom of sealed pouches made from the films under test. At set time intervals olfactory tests were conducted to determine the presence of onion odour.

Test Conditions

The Onion tests were conducted in an oven at 34° C. +/−1° C. All samples were conditioned at ambient conditions for not less than 4 hours before testing.

Results

The results are presented in Table 2 below.

In the table the following symbols have the following meanings:

✓: No Odour
X: Odour
XX: Strong Odour
XXX: Very Strong Odour
-: Not tested

TABLE 2

| | | Test Interval | | | | | |
|---|---|---|---|---|---|---|---|
| Ref | Initial | 10 mins | +1 hour | +2 hours | +3 hours | +4 hours | +5 hours |
| A | ✓ | ✓ | ✓ | ✓ | ✓ | ✓ | X |
| D | ✓ | ✓ | ✓ | ✓ | X | XX | — |
| E | ✓ | ✓ | XX | XX | — | — | — |

Summary/Comments

There was a concern that by stretching the film by vacuum forming to produce embodiments of the invention, the barrier properties of the pouch may become compromised.

This set of Odour testing was modified slightly from the standard in that olfactory tests were carried out at hourly intervals up to the standard test end point of +4 hours.

Odour breakthrough between the two and three hour time period indicates that the barrier layer on the film having a thickness of 100 μm has been adversely affected by the vacuum forming process when the process is used to produce a 10 mm draw depth—i.e. a corrugation having a height of 10 mm from peak to trough.

Further odour testing of vacuum formed film having a thickness of 100 μm was carried out and details of the further testing are set out below:

Purpose of Evaluation

To carry out an odour analysis of a film having a thickness of 100 μm and improved odour barrier Sealed Air film having a thickness of 75 μm vacuum formed to a 5 mm depth of draw.

Conclusion

From the Onion Odour Test results the draw depth alteration from 10 mm (see report below) to 5 mm has made a significant difference and hasn't (apart from samples E6 and E7) compromised the barrier layer in either the film having a thickness of 100 μm or film having a thickness of 75 μm.

Samples

The samples tested are shown in Table 3.

In the table, "Ref" corresponds to a reference for each sample. "Profile Type" corresponds to the profile types shown in FIG. 1. "Setting" corresponds to the setting for vacuum forming 1=Low Temperature, 2=Low/Medium Temperature, 3=Medium/High Temperature, 4=High Temperature, FULL=highest possible temperature. "Dwell Time" indicates the length of draw of vacuum forming in seconds. "Film" corresponds to the thickness of the material used for production of the bag in micrometers.

TABLE 3

| Ref | Profile Type | Setting | Dwell Time | Film | Comments |
|---|---|---|---|---|---|
| A1 | 1 | 1 | 10 s | 100 | Discontinued dwell timings of 3 |
| A2 | 2 | 1 | 10 s | 100 | and 5 s due to limited draw |
| A3 | 3 | 1 | 10 s | 100 | capacity |
| B1 | 1 | 2 | 10 s | 100 | Discontinued dwell timings of 3 |
| B2 | 2 | 2 | 10 s | 100 | and 5 s due to limited draw |
| B3 | 3 | 2 | 10 s | 100 | capacity |
| C1 | 1 | 3 | 5 s | 100 | Discontinued dwell timings of 3 s |
| C2 | 2 | 3 | 5 s | 100 | due to limited draw capacity |
| C3 | 3 | 3 | 5 s | 100 | |
| C4 | 1 | 3 | 10 s | 100 | Draw damaged film |
| C5 | 2 | 3 | 10 s | 100 | Draw damaged film |
| C6 | 3 | 3 | 10 s | 100 | |
| D1 | 1 | 4 | 3 s | 100 | |
| D2 | 2 | 4 | 3 s | 100 | |
| D3 | 3 | 4 | 3 s | 100 | |
| D4 | 1 | 4 | 5 s | 100 | Draw damaged film |
| D5 | 2 | 4 | 5 s | 100 | |
| D6 | 3 | 4 | 5 s | 100 | |
| D7 | 1 | 4 | 10 s | 100 | |
| D8 | 2 | 4 | 10 s | 100 | |

TABLE 3-continued

| Ref | Profile Type | Setting | Dwell Time | Film | Comments |
|---|---|---|---|---|---|
| D9 | 3 | 4 | 10 s | 100 | |
| E1 | 1 | FULL | 3 s | 100 | Draw damaged film |
| E2 | 2 | FULL | 3 s | 100 | Draw damaged film |
| E3 | 3 | FULL | 3 s | 100 | |
| E4 | 1 | FULL | 5 s | 100 | Draw damaged film |
| E5 | 2 | FULL | 5 s | 100 | |
| E6 | 3 | FULL | 5 s | 100 | |
| E7 | 1 | FULL | 10 s | 100 | |
| E8 | 2 | FULL | 10 s | 100 | |
| E9 | 3 | FULL | 10 s | 100 | |
| F1 | 3 | FULL | 10 s | 75 | Discontinued dwell timings below 10 s due to limited draw capacity |
| F2 | 3 | 1 | 15 s | 75 | |
| F3 | 3 | 2 | 15 s | 75 | |
| F4 | 3 | 3 | 15 s | 75 | |
| F5 | 3 | 4 | 15 s | 75 | |
| F6 | 3 | FULL | 15 s | 75 | |

Test Method and Programme
Odour Test

Determination of odour transmission of colostomy and ileostomy bags (tested in accordance with the standard test described in BS IS08670-3:2000) was conducted.

Test Conditions

The Onion tests were conducted in an oven at 34° C. +/−1° C. All samples were conditioned at ambient conditions for not less than 4 hours before testing.

Results
Onion Odour Test

Samples of onion (20.0 g+/−2 g) were placed in the bottom of sealed pouches made from the films under test. At set time intervals olfactory tests were conducted to determine the presence of onion odour.

The results are presented in Table 4.

In the table the following symbols have the following meanings:
✓: No Odour
X: Odour
XX: Strong Odour
XXX: Very Strong Odour
-: Not tested

TABLE 4

| | Test Interval | | | | | | |
|---|---|---|---|---|---|---|---|
| Ref | Initial | 10 mins | +1 hour | +2 hours | +3 hours | +4 hours | +5 hours |
| A1 | ✓ | ✓ | ✓ | ✓ | ✓ | ✓ | ✓ |
| A2 | ✓ | ✓ | ✓ | ✓ | ✓ | ✓ | ✓ |
| A3 | ✓ | ✓ | ✓ | ✓ | ✓ | ✓ | ✓ |
| B1 | ✓ | ✓ | ✓ | ✓ | ✓ | ✓ | ✓ |
| B2 | ✓ | ✓ | ✓ | ✓ | ✓ | ✓ | ✓ |
| B3 | ✓ | ✓ | ✓ | ✓ | ✓ | ✓ | ✓ |
| C1 | ✓ | ✓ | ✓ | ✓ | ✓ | ✓ | ✓ |
| C2 | ✓ | ✓ | ✓ | ✓ | ✓ | ✓ | ✓ |
| C3 | ✓ | ✓ | ✓ | ✓ | ✓ | ✓ | ✓ |
| C4 | — | — | — | — | — | — | — |
| C5 | — | — | — | — | — | — | — |
| C6 | ✓ | ✓ | ✓ | ✓ | ✓ | ✓ | ✓ |
| D1 | ✓ | ✓ | ✓ | ✓ | ✓ | ✓ | ✓ |
| D2 | ✓ | ✓ | ✓ | ✓ | ✓ | ✓ | ✓ |
| D3 | ✓ | ✓ | ✓ | ✓ | ✓ | ✓ | ✓ |
| D4 | — | — | — | — | — | — | — |
| D5 | ✓ | ✓ | ✓ | ✓ | ✓ | ✓ | ✓ |
| D6 | ✓ | ✓ | ✓ | ✓ | ✓ | ✓ | ✓ |
| D7 | ✓ | ✓ | ✓ | ✓ | ✓ | ✓ | ✓ |
| D8 | ✓ | ✓ | ✓ | ✓ | ✓ | ✓ | ✓ |
| D9 | ✓ | ✓ | ✓ | ✓ | ✓ | ✓ | ✓ |
| E1 | — | — | — | — | — | — | — |
| E2 | — | — | — | — | — | — | — |
| E3 | ✓ | ✓ | ✓ | ✓ | ✓ | ✓ | ✓ |
| E4 | — | — | — | — | — | — | — |
| E5 | ✓ | ✓ | ✓ | ✓ | ✓ | ✓ | ✓ |
| E6 | ✓ | ✓ | X | — | — | — | — |
| E7 | ✓ | ✓ | X | — | — | — | — |
| E8 | ✓ | ✓ | ✓ | ✓ | ✓ | ✓ | ✓ |
| E9 | ✓ | ✓ | ✓ | ✓ | ✓ | ✓ | ✓ |
| F1 | ✓ | ✓ | ✓ | ✓ | ✓ | ✓ | ✓ |
| F2 | ✓ | ✓ | ✓ | ✓ | ✓ | ✓ | ✓ |
| F3 | ✓ | ✓ | ✓ | ✓ | ✓ | ✓ | ✓ |
| F4 | ✓ | ✓ | ✓ | ✓ | ✓ | ✓ | ✓ |
| F5 | ✓ | ✓ | ✓ | ✓ | ✓ | ✓ | ✓ |
| F6 | ✓ | ✓ | ✓ | ✓ | ✓ | ✓ | ✓ |

The results indicate that vacuum forming of the films tested to a draw depth of 5 mm achieved remarkably superior results compared to films tested to a draw depth of 10 mm.

The above described embodiments have been given by way of example only, and the skilled reader will naturally appreciate that many variations could be made thereto without departing from the scope of the claims.

The invention claimed is:

1. An ostomy bag having an inlet leading to a waste collection space defined by two opposing surfaces of two walls, a front wall and a rear wall, the inlet defined in the rear wall, the opposing surfaces configured to separate on the introduction of waste through the inlet and including at least one arcuate corrugation in the front wall opposing the inlet and no corrugation is provided in the rear wall defining the inlet, wherein the arcuate corrugation on the front wall is provided proximal to or only at the bottom of the bag and distal to top of the bag, and no corrugation is provided proximal to or at the top of the bag, wherein the walls are welded together at their edges, and wherein the height of the corrugation tapers from a maximum height proximal to the bottom of the bag to a minimum height distal to the bottom of the bag.

2. The ostomy bag according to claim 1, wherein a mounting plate abuts the inlet.

3. The ostomy bag according to claim 1, wherein the corrugation comprises a ridge in a first wall of the bag which extends outwardly away from the opposing surface of the bag.

4. The ostomy bag according to claim 1, wherein the corrugation is deformable under weight of the waste in the bag.

5. The ostomy bag according to claim 1, wherein the corrugation is substantially parallel with the edges of the opposing walls of the bag.

6. The ostomy bag according to claim 1, wherein the corrugation is approximately arcuate and is located in a sector defined in a lower portion of the bag.

7. The ostomy bag according to claim 1, wherein the bag is defined by an ellipse, having an upper focus, a lower focus, an upper vertex and a lower vertex.

8. The ostomy bag according to claim 7, wherein the corrugation is located in a major sector of the ellipse wherein the major sector is approximately defined by a chord through the upper focus or top of the major sector is defined by two lines extending from the upper focus to points equidistant from the upper vertex and wherein the lines are above a chord through the upper focus.

9. The ostomy bag according to claim 7, wherein the inlet leading to a waste collection space is approximately aligned with the upper focus.

10. The ostomy bag according to claim 1, wherein the corrugation comprises a ridge having a height of about 5 mm and a width of about 5 mm.

11. The ostomy bag according to claim 1, wherein a plurality of parallel corrugations are provided.

12. The ostomy bag according to claim 1, wherein four corrugations are provided.

13. A method of producing an ostomy bag according to claim 1 wherein the at least one corrugation is formed by heat and vacuum.

\* \* \* \* \*